United States Patent
Knippelmeyer et al.

(10) Patent No.: US 8,384,029 B2
(45) Date of Patent: Feb. 26, 2013

(54) CROSS-SECTION SYSTEMS AND METHODS

(75) Inventors: Rainer Knippelmeyer, Munich (DE); Lawrence Scipioni, Bedford, MA (US); Christoph Riedesel, Aalen (DE); John Morgan, Marblehead, MA (US); Ulrich Mantz, Schelklingen (DE); Ulrich Wagemann, Aalen (DE)

(73) Assignee: Carl Zeiss NTS, LLC, Peabody, MA (US)

(*) Notice: Subject to any disclaimer, the term of this patent is extended or adjusted under 35 U.S.C. 154(b) by 47 days.

(21) Appl. No.: 12/994,344

(22) PCT Filed: Jun. 16, 2009

(86) PCT No.: PCT/US2009/047474
§ 371 (c)(1),
(2), (4) Date: Jun. 9, 2011

(87) PCT Pub. No.: WO2009/155272
PCT Pub. Date: Dec. 23, 2009

(65) Prior Publication Data
US 2012/0085906 A1    Apr. 12, 2012

Related U.S. Application Data

(60) Provisional application No. 61/074,361, filed on Jun. 20, 2008.

(51) Int. Cl.
*G01N 1/28* (2006.01)
*G01N 23/00* (2006.01)
*H01L 21/44* (2006.01)

(52) U.S. Cl. ..... 250/306; 250/307; 250/310; 250/492.2; 250/402.3; 216/59; 216/66; 850/33; 73/863; 73/864.91; 382/145; 438/487

(58) Field of Classification Search .......... 250/306, 250/307, 310, 492.2, 492.3; 216/59, 66; 850/33; 73/863, 864.91; 382/145; 438/487
See application file for complete search history.

(56) References Cited

U.S. PATENT DOCUMENTS

| | | | |
|---|---|---|---|
| 6,838,668 B2 * | 1/2005 | Berger et al. | 850/9 |
| 6,885,109 B2 * | 4/2005 | Yamaguchi | 257/787 |
| 7,160,475 B2 * | 1/2007 | Scipioni | 216/2 |
| 2003/0098416 A1 | 5/2003 | Shemesh et al. | |
| 2004/0065826 A1 | 4/2004 | Berger et al. | |
| 2005/0178980 A1 | 8/2005 | Skidmore et al. | |
| 2006/0060777 A1 | 3/2006 | Motoi | |
| 2007/0057182 A1 | 3/2007 | Feuerbaum | |
| 2007/0158558 A1 | 7/2007 | Ward et al. | |
| 2011/0006298 A1 * | 1/2011 | Aburaya et al. | 257/43 |

FOREIGN PATENT DOCUMENTS

| | | |
|---|---|---|
| EP | 0 643 297 | 3/1995 |
| EP | 0 734 045 | 9/1996 |

OTHER PUBLICATIONS

International Search Report and a Written Opinion from the counterpart PCT Application No. PCT/US2009/047474, dated Jan. 27, 2010.

* cited by examiner

*Primary Examiner* — Nikita Wells
(74) *Attorney, Agent, or Firm* — Fish & Richardson P.C.

(57) ABSTRACT

A first instrument (230) is used to image a first semiconductor article having a trench (110) of defined cross-section, while a second instrument (220) is used to simultaneously prepare a second semiconductor article with a trench of defined cross-section. Furthermore, a method is disclosed to prepare a trench (110) of defined cross-section in a semiconductor article by rough milling and subsequent fine milling.

14 Claims, 5 Drawing Sheets

CROSS-SECTION SYSTEMS AND METHODS

TECHNICAL FIELD

This disclosure relates to cross-section systems and methods.

BACKGROUND

Techniques are known to form the cross-section of a sample, such as a semiconductor article, and to subsequently inspect and/or modify an area of interest at or near the cross-section of the sample.

SUMMARY

Generally, the disclosure relates to preparing and imaging cross-sections of samples, as well as related systems and components. In some embodiments, a sample can be a semiconductor article. In general, the methods can enhance throughput and/or efficiency.

In one aspect, the disclosure generally features a method that includes imaging a cross-section of a first sample, and simultaneously preparing a cross-section of a second sample so that the cross-section of the second sample can be imaged.

In another aspect, the disclosure generally features a method that includes using a gas field ion microscope to image a cross-section of a first sample, and, simultaneously with imaging the cross-section of the first sample, preparing a cross-section of each of a first plurality of samples so that the cross-section of each of the first plurality of samples can be imaged. The method also includes, after imaging the cross-section of the first sample, imaging the cross-section of at least one of the first plurality of samples, and, simultaneously with imaging the cross-section of the at least one of the first plurality of samples, preparing a cross-section of a second plurality of samples so that the cross-section of each of the second plurality of samples can be imaged. The first plurality of samples excludes the first sample, and the second plurality of samples excludes the first plurality of samples.

In a further aspect, the disclosure generally features a system that includes a first instrument configured to image a cross-section of a first sample, and a second instrument configured so that, while the first instrument images the first sample, the second instrument prepares a cross-section of a second sample.

In an additional aspect, the disclosure generally features a method that includes preparing a first cross-section of a sample, the first cross-section having a first roughness, and modifying the first cross-section of the sample to provide a second cross-section of the sample, the second cross-section having a second roughness.

In another aspect, the disclosure generally features a method that includes using a first apparatus to prepare a first cross-section of a sample, and using a second apparatus to modify the first cross-section of the sample to provide a second cross-section of the sample, the second apparatus being different from the first apparatus.

In a further aspect, the disclosure generally features a system that includes a first apparatus configured to prepare a first cross-section of a sample, where the first cross-section has a first roughness. The system also includes a second apparatus configured to modify the first cross-section of the sample to provide a second cross-section of the sample. The second cross-section has a second roughness that is different from the first roughness, and the second apparatus is different from the first apparatus.

Other features and advantages will be apparent from the description, drawings, and claims.

DESCRIPTION OF DRAWINGS

Like reference symbols in the various drawings indicate like elements.

DETAILED DESCRIPTION

Introduction

Semiconductor fabrication typically involves the preparation of an article (a semiconductor article) that includes multiple layers of materials sequentially deposited and processed to form an integrated electronic circuit, an integrated circuit element, and/or a different microelectronic device. Such articles typically contain various features (e.g., circuit lines formed of electrically conductive material, wells filled with electrically non-conductive material, regions formed of electrically semiconductive material) that are precisely positioned with respect to each other (e.g., generally on the scale of within a few nanometers). The location, size (length, width, depth), composition (chemical composition) and related properties (conductivity, crystalline orientation, magnetic properties) of a given feature can have an important impact on the performance of the article. For example, in certain instances, if one or more of these parameters is outside an appropriate range, the article may be rejected because it cannot function as desired. As a result, it is generally desirable to have very good control over each step during semiconductor fabrication, and it would be advantageous to have a tool that could monitor the fabrication of a semiconductor article at various steps in the fabrication process to investigate the location, size, composition and related properties of one or more features at various stages of the semiconductor fabrication process. As used herein, the term semiconductor article refers to an integrated electronic circuit, an integrated circuit element, a microelectronic device or an article formed during the process of fabricating an integrated electronic circuit, an integrated circuit element, a microelectronic device. In some embodiments, a semiconductor article can be a portion of a flat panel display or a photovoltaic cell.

Regions of a semiconductor article can be formed of different types of material (electrically conductive, electrically non-conductive, electrically semiconductive). Exemplary electrically conductive materials include metals, such as aluminum, chromium, nickel, tantalum, titanium, tungsten, and alloys including one or more of these metals (e.g., aluminum-copper alloys). Metal silicides (e.g., nickel silicides, tantalum silicides) can also be electrically conductive. Exemplary electrically non-conductive materials include borides, carbides, nitrides, oxides, phosphides, and sulfides of one or more of the metals (e.g., tantalum borides, tantalum germaniums, tantalum nitrides, tantalum silicon nitrides, and titanium nitrides). Exemplary electrically semiconductive materials include silicon, germanium and gallium arsenide. Optionally, an electrically semiconductive material can be doped (p-doped, n-doped) to enhance the electrical conductivity of the material.

Typical steps in the deposition/processing of a given layer of material include imaging the article (e.g., to determine where a desired feature to be formed should be located), depositing an appropriate material (e.g., an electrically conductive material, an electrically semiconductive material, an electrically non-conductive material) and etching to remove unwanted material from certain locations in the article. Often, a photoresist, such as a polymer photoresist, is deposited/exposed to appropriate radiation/selectively etched to assist in controlling the location and size of a given feature. Typically, the photoresist is removed in one or more subsequent process steps, and, in general, the final semiconductor article desirably does not contain an appreciable amount of photoresist.

Semiconductor articles can be inspected using, for example, charged particles, such as electrons and/or ions. In some instances, to achieve such inspection, a cross-section of the article is made to expose an area of interest of the article, followed by the inspection process. In some instances, the absolute and relative time periods to cut semiconductor article to form a cross-section of the article, and to subsequently inspect the article can vary. Often, however, cutting the article to form the cross-section can take substantially more time than inspecting the article. Generally, the process of preparing a cross-section on a semiconductor article using a beam column takes a longer period of time than the process of imaging the cross-section. For example, it can take on the order of several minutes to a few hours (e.g., three minutes, five minutes, 10 minutes, 20 minutes, 30 minutes, one hour, two hours) to prepare a cross-section of a semiconductor article, whereas inspecting a semiconductor article generally takes a minute or less (e.g., one minute, 50 seconds, 40 seconds, 30 seconds, 20 seconds, 10 seconds). In some instances, it can take at least two times as long (e.g., at least three times as long, at least four times as long, at least five times as long, at least six times as long, at least seven times as long, at least eight times as long, at least nine times as long, at least ten times as long) to cut as a semiconductor article to form its cross-section as it does to inspect the semiconductor article.

Accordingly, the disclosure provides processes that can reduce the impact of this time disparity. In some embodiments, this is achieved by simultaneously cutting a cross-section into each of multiple semiconductor articles (parallel processing), followed by inspecting the articles in series (serial processing). In certain embodiments, this is achieved by using multiple different cutting devices to form the cross-section of a semiconductor article (e.g., a first device to make a relatively rough cross-section and a second device to form the relatively rough cross-section into a relatively smooth cross-section). Optionally, these approaches can be combined.

Semiconductor Article Cross-Section

Figure 1A:
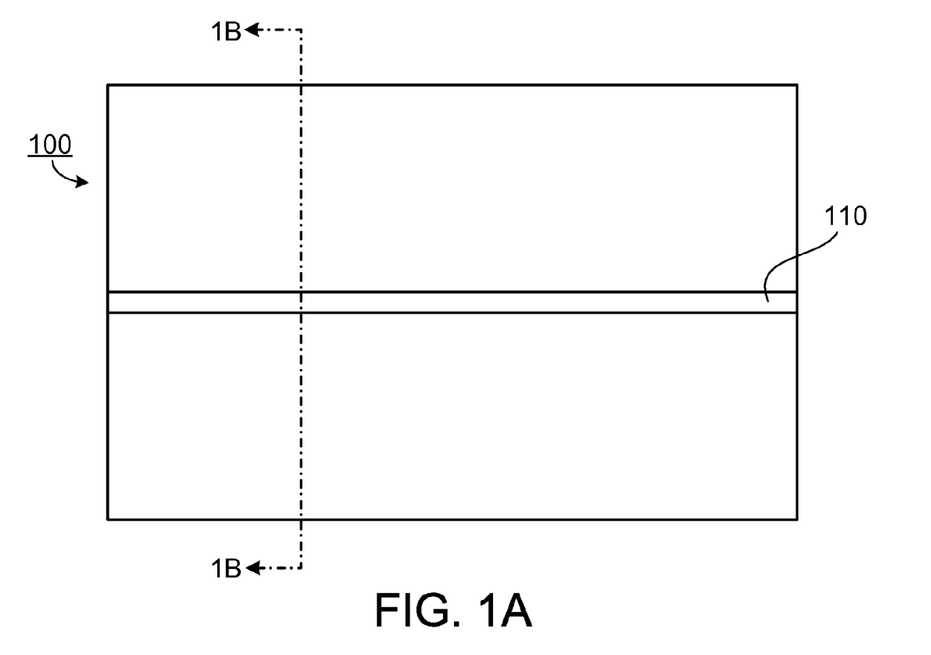
FIGS. 1A and 1B show partial top and cross-sectional views, respectively, of a semiconductor article having a cut cross-section.
Figure 1B:
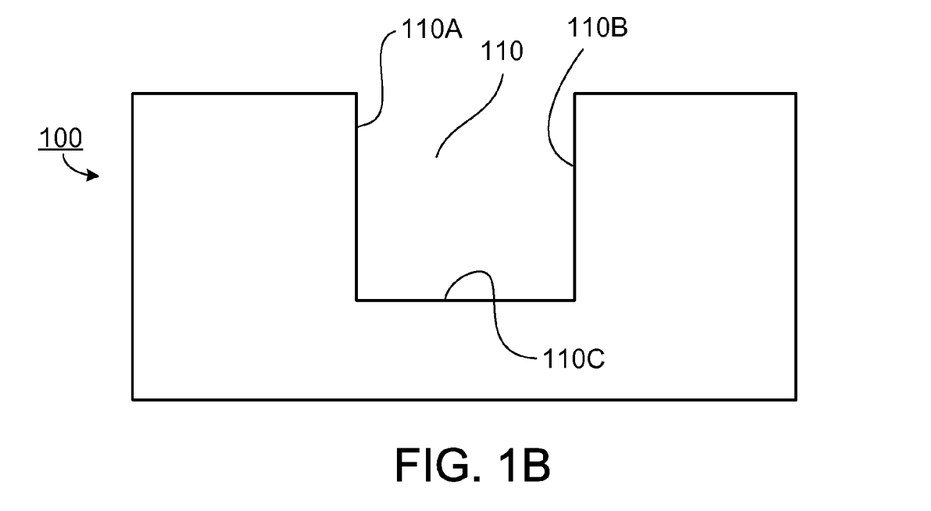

FIGS. 1A and 1B show partial top and cross-sectional views, respectively of a semiconductor article 100. As shown in FIG. 1B, article 100 has been cut to expose a cross-section 110 with sidewalls 110A and 110B and bottom wall 110C. Although not shown in FIGS. 1A and 1B, semiconductor article 100 includes many layers of different materials, and, in some instances, multiple different materials within the same layer.

Systems and Processes

Figure 2:
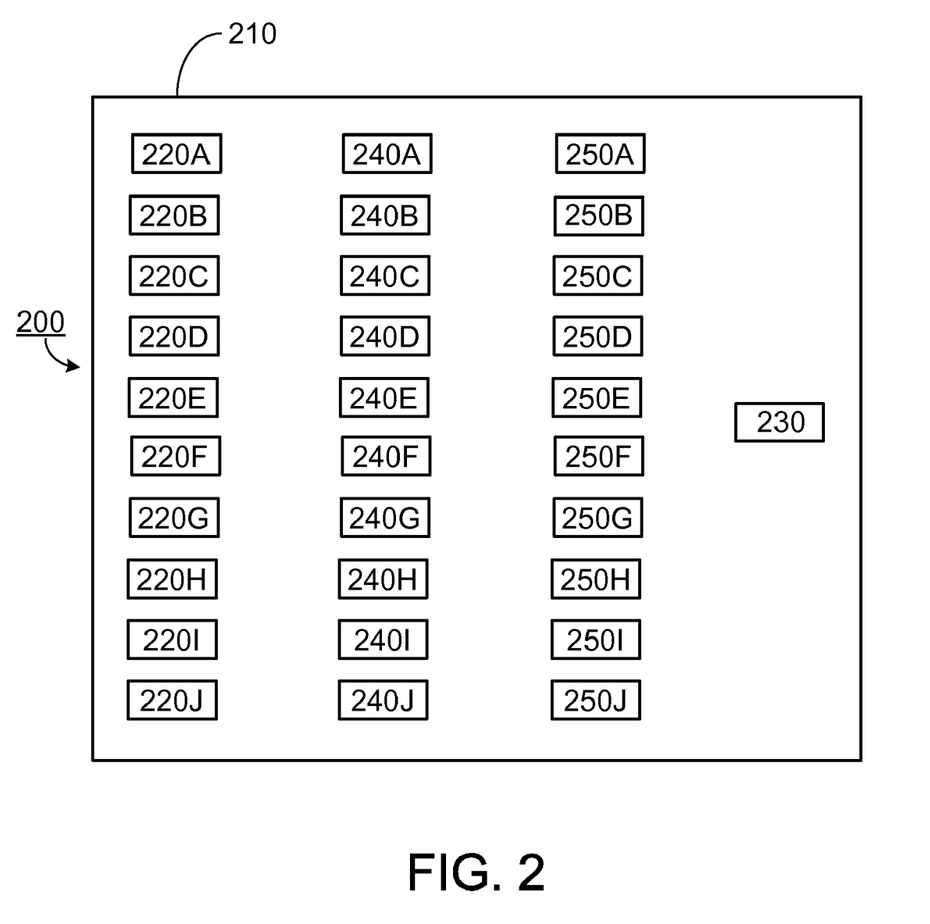
FIG. 2 is a schematic representation of a system that can be used to cut a cross-section of a sample and inspect the sample.

FIG. 2 is a schematic representation of a sample handling system 200 having a housing 210, devices 220A-220J designed to cut a cross-section of a sample, a device 230 designed to inspect a sample, and sample holders 240A-240J. As discussed below, system 200 optionally includes sample holders 250A-250J. While depicted in FIG. 2 as being housed in a single housing, in some embodiments, one or more of devices 220A-220J can be in a different housing from device 26.

During use, each holder 240A-240J has a respective semiconductor article disposed therein/thereon, and holders 240A-240J are positioned adjacent corresponding devices 220A-220J. Devices 220A-220J are then simultaneously activated so that each device cuts a cross-section into the semiconductor article disposed in/on its corresponding sample holder 240A-240J. Devices 220A-220J can be, for example, liquid metal ion devices (e.g., focused liquid metal ion beam devices, such as Ga focused ion beam devices), gas field ion beam devices, electron beam devices, laser beam devices or plasma ion sources. Such devices are generally well known to those skilled in the art. Examples of gas field ion beam devices are disclosed, for example, in US 2007-0158558, which is hereby incorporated by reference. Combinations of different devices can be used.

After a cross-section is cut into each sample by its corresponding device 220A-220J, the samples are moved in series by their corresponding holders 240A-240J so that each sample is ultimately inspected by device 230. Device 230 can be, for example, a gas field ion microscope (e.g., a He ion microscope), an electron microscope (e.g., a scanning electron microscope), laser scanning microscope, scatterometry device or ellipsometer.

Typically, holders 240A-240J are operably connected to one or more corresponding robotic arms or other devices that effect the desired movement of the holder within system 200.

In some embodiments, system 200 includes a second series of sample holders 250A-250J, each configured to hold a sample. With this arrangement, as device 230 is serially inspecting the samples in holders 240A-240J, additional samples, each of which is in a corresponding holder 250A-250J, are positioned to have a cross-section cut therein by devices 220A-220J. Optionally, holders 240A-240J may be configured to position a first series of samples to be simultaneously cut by devices 220A-220J while also being able to position a second series of samples to be serially inspected by device 230, in which case system 200 may not include holders 250A-250J.

Figure 3:
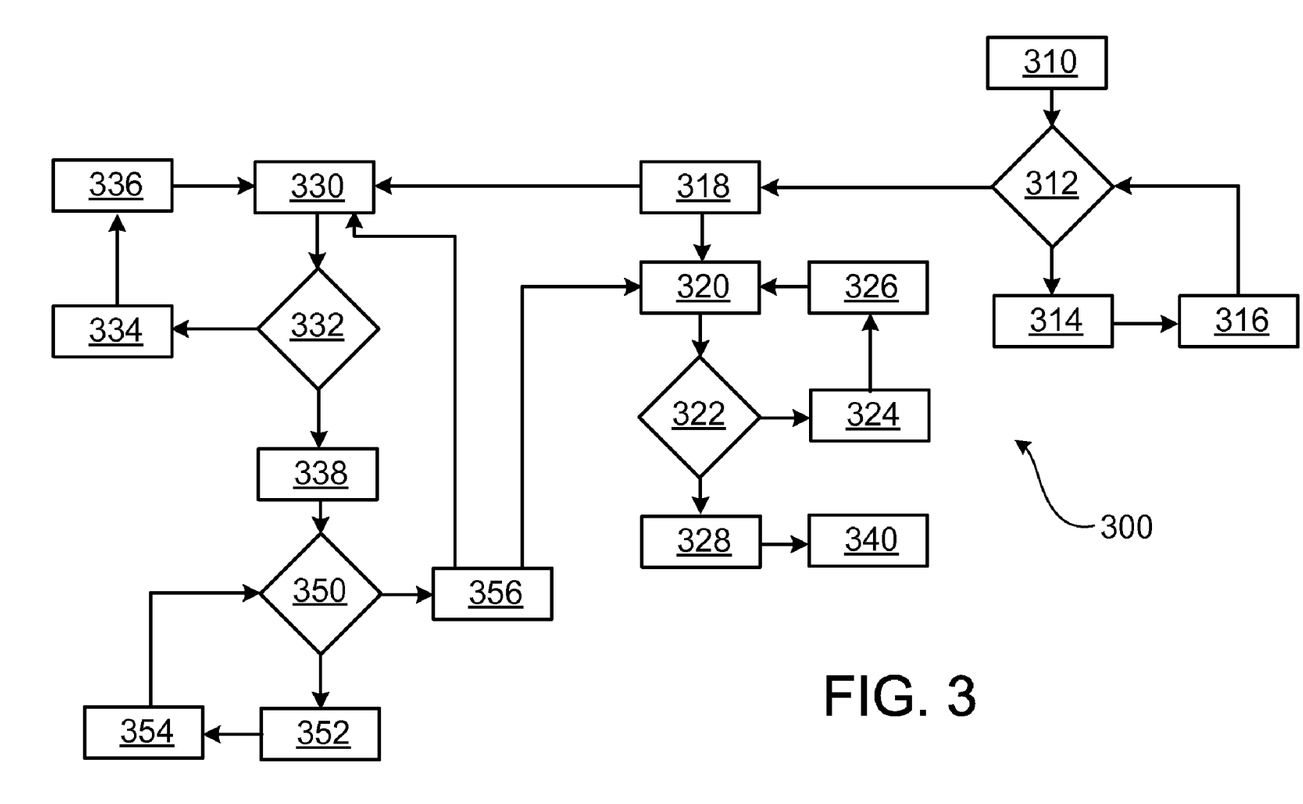
FIG. 3 is a process flow chart.

FIG. 3 is a flow chart of a process 300. In step 310, the cross-section is cut for a collection of samples. In step 312, the question is asked whether the cutting is complete. At step 314, the answer is no, and at step 316 cutting of the samples is continued, followed by a return to step 312. At step 318, the answer to the question at step 312 is yes, and the samples are then serially inspected at step 320. At step 322, the question is asked whether all the samples have been inspected. At step 324, the answer is no, and the samples continue to be inspected at step 326, followed by a return to step 320. At step 328, the answer to the question at step 322 is yes, and the inspected samples are moved to the next stage in the process at step 340. Returning again to step 318 (answer to the question at step 312 is yes), the cross-section for another collection of samples is cut at step 330. At step 332, the question is asked whether the cutting is complete. At step 334, the answer is no, and at step 336 cutting of the samples is continued, followed by a return to step 330. At step 338, the answer to the question at step 332 is yes, and at step 350 the question is asked whether inspection of the prior collection of samples is complete. At step 352, the answer is no, and at step 354 a wait time is initiated, followed by a return to step 350. At step 356, the answer to the question at step 350 is yes, and the cut samples are then inspected at step 320. In addition, at step 356 (answer to question at step 350 is yes), the cross-section for another collection of samples is cut at step 330. The process of simultaneously cutting a collection of multiple samples while at the same time serially inspecting a different collection of multiple samples is repeated as many times as desired.

Figure 4:
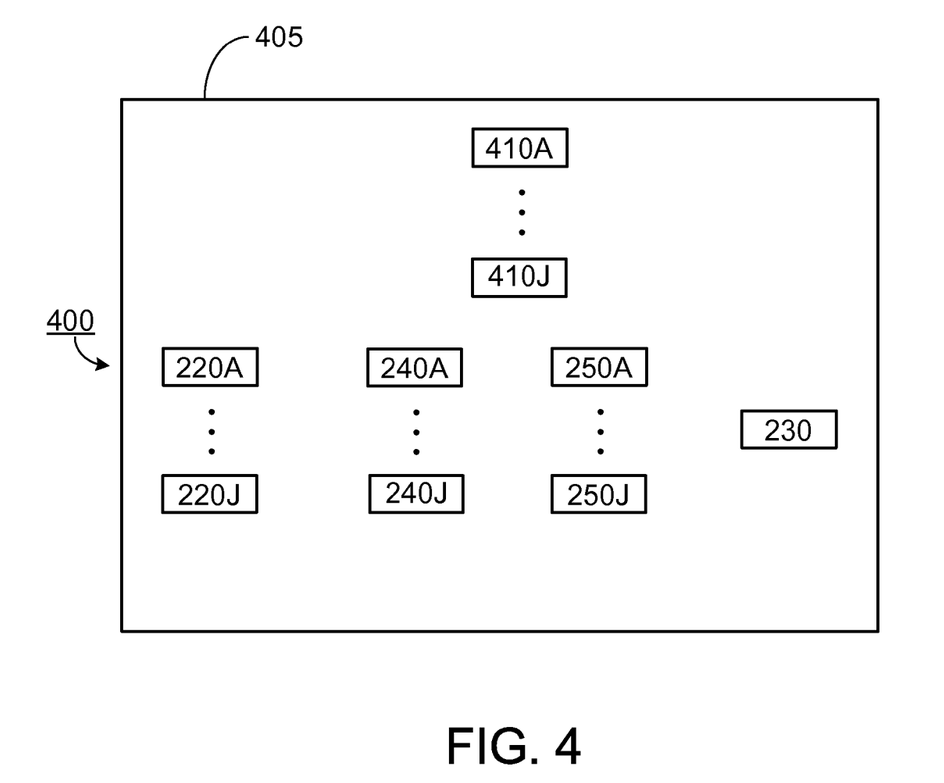
FIG. 4 is a schematic representation of a system that can be used to cut a cross-section of a sample and inspect the sample.

FIG. 4 shows a system 400 with a housing 405 that further includes devices 410A-410J designed to cut a cross-section of a sample. In system 400, devices 220A-220J can be used to provide an initial, relatively rough cross-section cut in each of the samples, and devices 410A-410J can subsequently provide a relatively smooth (more refined) cross-section cut in each corresponding sample. An advantage to this arrangement relates to the realization that making a relatively smooth cross-section cut in sample can take substantially more time than making a relatively rough cross-section cut in sample. Thus, relative to a process that involves making the relatively smooth cross-section using a single tool that is capable of providing a relatively smooth cross-section, the amount of time involved with preparing the final cross-section of a sample can be reduced by using a first device that quickly provides a relatively rough cross-section, followed by using a second device that provides a more refined (smoother) cross-section. In general, devices 410A-410J can be selected from the list of cutting devices noted above with respect to devices 220A-220J. In general, one or more of devices 220A-220J can be the same as or different from one or more of devices 410A-410J. In some embodiments, devices 220A-220J are Ga focused ion beam devices, and devices 410A-410J are gas field ion microscopes (e.g., He ion microscopes) or scanning electron microscopes.

Figure 5:
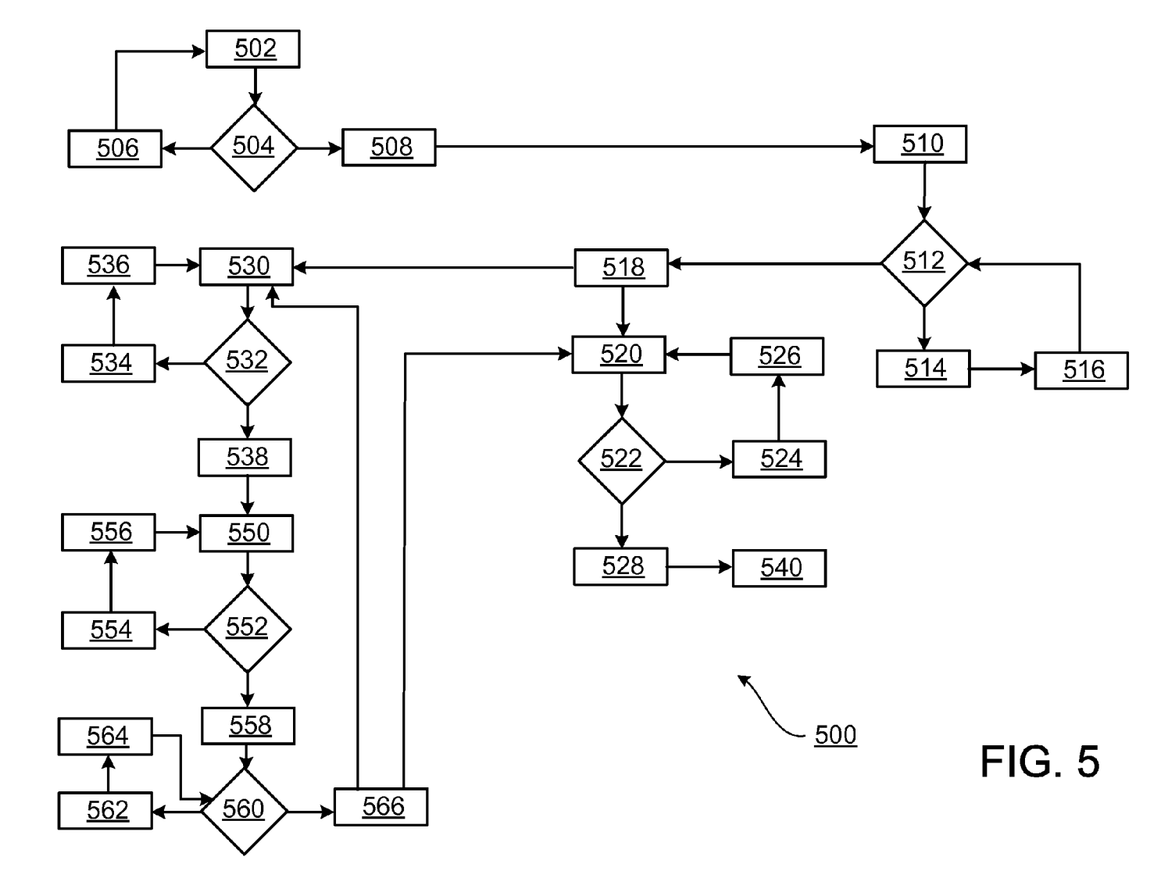
FIG. 5 is a process flow chart.

FIG. 5 is a flow chart of a process 500. The process involves a step 502 where the relatively rough cross-section is cut for a collection of samples. In step 504, the question is asked whether the relatively rough cutting is complete. If the answer is no, at step 506, the relatively rough cutting of the samples is continued, followed by a return to step 502. At step 508, the answer to step 504 is yes, and the refined (relatively smooth) cross-section is cut for the collection of samples at step 510. In step 512, the question is asked whether the refined (relatively smooth) cutting is complete. At step 514, the answer is no, and at step 516 refined (relatively smooth) cutting of the samples is continued, followed by a return to step 512. At step 518, the answer to the question at step 512 is yes, and the samples are then serially inspected at step 520. At step 522, the question is asked whether all the samples have been inspected. At step 524, the answer is no, and the samples continue to be inspected at step 526, followed by a return to step 520. At step 528, the answer to the question at step 522 is yes, and the inspected samples are moved to the next stage in the process at step 540. Returning again to step 518 (answer to the question at step 512 is yes), the relatively rough cross-section for another collection of samples is cut at step 530. At step 532, the question is asked whether the relatively rough cutting is complete. At step 534, the answer is no, and at step 536 relatively rough cutting of the samples is continued, followed by a return to step 530. At step 538, the answer to the question at step 530 is yes, and the refined (relatively smooth) cross-section is cut for the collection of samples at step 550. In step 552, the question is asked whether the refined (relatively smooth) cutting is complete. At step 554, the answer is no, and at step 556 refined (relatively smooth) cutting of the samples is continued, followed by a return to step 552. At step 558, the answer to the question at step 552 is yes, and at step 560 then the question is asked whether inspection of the prior collection of samples is complete. At step 562, the answer is no, and at step 564 a wait time is initiated, followed by a return to step 560. At step 566, the answer to the question at step 560 is yes, and the cut samples are then inspected at step 520. In addition, at step 556 (answer to question at step 560 is yes), the rough cross-section for another collection of samples is cut at step 530. The process of simultaneously cutting a collection of multiple samples (relatively rough cut followed by relatively smooth cut) while at the same time serially inspecting a different collection of multiple samples is repeated as many times as desired.

In some embodiments, after the relatively rough cut, the cross-section of a sample has a roughness that is at least two times (e.g., at least three times, at least five times, at least 10 times), and/or up to 100 times (e.g., up to 100 times) the roughness of the cross-section after the refined (relatively smooth) cut. In certain embodiments, preparing the rough cross-section of the sample takes at least two times (e.g., at least three less, at least four times less, at least five times less) time than preparing the refined (relatively smooth) cross-section of the sample.

In some embodiments, there can be a period of time (a pause) between preparing the rough cross-section of the sample and preparing the refined (relatively smooth) cross-section of the sample. This period of time can be, for example, from five seconds to five minutes (e.g., at least 30 seconds, at least one minute).

In the foregoing description, reference is made to inspection of a semiconductor article.

An example of such detection involves the detection of voids. During the fabrication of a semiconductor article, voids in certain features or layers may be inadvertently formed. In some embodiments, the voids can undesirably impact the properties (e.g., electrical, mechanical) of the feature and/or the overall device. Subsequent processing steps may open the void, and the void may, for example, fill with liquid and/or gaseous components. This can cause corrosion of the underlying structures, particle defects and/or residue defects on the surrounding wafer surface. Ultimately, the presence of voids can result in deviation of electrical and/or mechanical properties from desired (e.g., designed) values.

Another example of the defect detection of a semiconductor article involves overlay shift registration. Overlay shift registration generally refers to the alignment of a feature of a given layer of a semiconductor article with a feature in a different layer of the semiconductor article. As noted above, the formation of a semiconductor article generally involves the proper formation of many layers. Typically, a semiconductor article contains well over 20 layers. Often, each layer can contain multiple different features, each of which is desirably located with high precision so that the semiconductor article can function properly. As an example, a semiconductor article can contain lateral features, such as electrically conductive wires, which are in different layers and connected to each other by a via. In general, it is desirable to have features within the semiconductor article properly aligned with each other.

An additional example of defect detection involves critical dimension metrology. Critical dimension metrology refers to the measurement of the linear dimensions of features in a semiconductor article that can have a critical impact on the performance of the device. Examples of such features can include lines (e.g., lines of electrically conductive material, lines of electrically semiconductive conductive material, lines of electrically non-conductive material). A semiconductor article can contain one or more features having a size dimension of 20 nm or less (e.g., 10 nm or less, five nm or less, four nm or less, three nm or less, two nm or less, one nm or less). In some embodiments, the size of the feature is measured multiple times to provide statistical information regarding the size of the feature. Critical dimension measurements frequently involve, e.g., the determination of the length of a patterned feature on a wafer, for example. Wafers (containing multiple dies, with each die forming a semiconductor article)

may be selected at random from a fabrication line for inspection, or all wafers on the line can be inspected. An imaging instrument can be used to measure selected critical dimensions at a relatively high throughput rate. If the measured critical dimension does not fall within acceptable limits, the wafer may be discarded. If multiple samples originating from a particular fabrication machine have critical dimensions outside acceptable limits, the machine may be taken out of service, or its operating parameters changed.

A further example of defect detection involves line edge roughness and/or line width roughness. Line edge roughness generally refers to the roughness of the edge of a line of material in a semiconductor article, and line width roughness generally refers to the roughness of the width of a line of material in a semiconductor article. It can be desirable to understand these values to determine whether actual or potential problems exist in a given semiconductor article. For example, if adjacent lines formed of electrically conductive material have edges that bulge outward toward each other, the lines may contact each other resulting in a short. It can be desirable to understand the dimensions of line edge roughness and/or line width roughness to within five nm or less (e.g., four nm or less, three nm or less, two nm or less, one nm or less, 0.9 nm or less, 0.8 nm or less, 0.7 nm or less, 0.6 nm or less, 0.5 nm or less).

Examples of semiconductor article inspection are disclosed, for example, in US 2007-0158558.

Other Embodiments

While certain embodiments have been described, other embodiments are possible.

As an example, while a system has been described with 10 devices configured to cut a cross-section in an article, more generally, any number of such devices (e.g., one device, two devices, three devices, four devices, five devices, six devices, seven devices, eight devices, nine devices, 11 devices, 12 devices, etc.) can be used. In some embodiments, a system can be configured to include tens or even hundreds of cutting devices that are designed to work in parallel.

As an additional example, while embodiments have been described in which a single device is used to serially inspect a sample, in certain embodiments more than one (e.g., two, three, four, five, six, seven, eight, nine, 10, etc.) inspection device can be used. In some embodiments, a system can be configured to include tens or even hundreds of devices to inspect samples in series.

As a further example, while embodiments have been described in which one or more devices are used to inspect samples in series, in some embodiments, multiple devices can be used in parallel to inspect at least some (e.g., all) of the samples in parallel.

As another example, while embodiments have been described in which a system includes two different series of cutting devices (one series to make the relatively rough cut, and one series to make the relatively smooth cut), in some embodiments, more than two series (e.g., three series, four series, five series, six series, seven series, eight series, nine series, 10 series) of cutting devices may be used. In certain embodiments, the series of cutting devices are used serially to cut a cross-section in each of the samples. For example, in such embodiments, each series of cutting devices may make the surface of the cross-section cut smoother than the prior series of devices. In some embodiments, the series of cutting devices are used in parallel to cut a cross-section in various collections of samples. Optionally, combinations of serial and parallel configurations of series of cutting devices may be used.

As an additional example, while embodiments have been described in which different series of cutting devices are used in series or in parallel to cut cross-sections of samples, in some embodiments, a system can include a single cutting device to make the relatively cross-section cut and a single cutting device to make the relatively smooth cross-section cut. In general, in such systems, the devices are used in series (relatively rough then relatively smooth), followed by inspection of the sample.

As another example, while embodiments have been described in which samples are in the form of semiconductor articles, in some embodiments, other types of samples can be used. Examples include biological samples (e.g., tissue, nucleic acids, proteins, carbohydrates, lipids and cell membranes), pharmaceutical samples (e.g., a small molecule drug), frozen water (e.g., ice), read/write heads used in magnetic storage devices, and metal and alloy samples. Exemplary samples are disclosed in, for example, US 2007-0158558.

As a further example, while embodiments have been disclosed in which a sample is inspected, alternatively or additionally, the systems and methods can be used to modify (e.g., repair) a sample (e.g., to repair a region of the article at or near the portion of the article exposed by the cross-section). Such modification can involve gas assisted chemistry, which can be used to add material to and/or remove material to a sample (e.g., a given layer of the sample). As an example, gas assisted chemistry can be used for semiconductor circuit editing in which damaged or incorrectly fabricated circuits formed in semiconductor articles are repaired. Typically, circuit editing involves adding material to a circuit (e.g., to close a circuit that is open) and/or removing material from a circuit (e.g., to open a circuit that is closed). Gas assisted chemistry can also be used in photolithographic mask repair. Mask defects generally include an excess of mask material in a region of the mask where there should be no material, and/or an absence of mask material where material should be present. Thus, gas assisted chemistry can be used in mask repair to add and/or remove material from a mask as desired. Typically, gas assisted chemistry involves the use of a charged particle beam (e.g., ion beam, electron beam, both) that interacts with an appropriate gas (e.g., $Cl_2$, $O_2$, $I_2$, $XeF_2$, $F_2$, $CF_4$, $H_2O$, $XeF_2$, $F_2$, $CF_4$, $WF_6$). As another example, modification of a sample can involve sputtering. In some instances, when fabricating articles, it can be desirable during certain steps to remove materials (e.g., when removing undesired material from a circuit to edit the circuit, when repairing a mask). An ion beam can be used for this purpose where the ion beam sputters material from the sample. In particular, an ion beam generated via the interaction of gas atoms with a gas field ion source as described herein can be used for sputtering a sample. Although He gas ions may be used, it is typically preferable to use heavier ions (e.g., Ne gas ions, Ar gas ions, Kr gas ions, Xe gas ions) to remove material. During the removal of material, the ion beam is focused on the region of the sample where the material to be removed is located. Examples of such inspection are disclosed, for example, in US 2007-0158558.

In general, various aspects of the foregoing embodiments can be combined as desired.

Other embodiments are covered by the claims.

What is claimed is:

1. A method, comprising:
   using a first apparatus to prepare a first cross-section of a sample, the first cross-section having a first roughness; and
   using a second apparatus to modify the first cross-section of the sample to provide a second cross-section of the sample the second cross-section having a second roughness; wherein the first roughness is at least two times greater than the second roughness; and wherein, the second apparatus being different from the first apparatus.

2. The method of claim 1, wherein there is a period of time between preparing the first cross-section and modifying the cross-section.

3. The method of claim 1, wherein the first apparatus is elected from the group consisting of laser beam sources, plasma ion beam sources and liquid metal ion beam sources.

4. The method of claim 1, wherein the second apparatus comprises a gas field ion source.

5. The method of claim 1, further comprising, after preparing a first cross-section of a sample but before modifying the first cross-section of the sample, moving the sample.

6. The method of claim 1, wherein the second sample is a semiconductor article.

7. The method of claim 1, wherein the first apparatus and the second apparatus are housed in the same chamber.

8. A method, comprising:
preparing a first cross-section of a sample, the first cross-section having a first roughness, the first cross-section having sidewalls and a bottom wall; and
modifying the first cross-section of the sample to provide a second cross-section of the sample, the second cross-section having a second roughness different from the first roughness, the second cross-section having sidewalls and a bottom wall,
wherein a first apparatus is used to prepare the first cross-section of the sample, a second apparatus is used to prepare the second cross-section of the sample, and the second apparatus is different from the first apparatus.

9. A system, comprising:
a first apparatus configured to prepare a first cross-section of a sample, the first cross-section having a first roughness; and
a second apparatus configured to modify the first cross-section of the sample to provide a second cross-section of the sample, the second cross-section having a second roughness, wherein the first roughness is at least two times greater than the second roughness; and wherein the second apparatus is different from the first apparatus.

10. The system of claim 9, wherein the first apparatus is selected from the group consisting of laser beam sources, plasma ion beam sources and liquid metal ion beam sources.

11. The system of claim 9, wherein the second apparatus comprises a gas field ion source.

12. The system of claim 9, further comprising a third apparatus different from the first and second apparatuses, the third apparatus being configured to inspect the sample.

13. The system of claim 9, comprising a chamber, and the first apparatus and the second apparatus are housed in the chamber.

14. A method, comprising:
using a gas field ion microscope to image a cross-section of a first sample, the cross-section of the first sample having sidewalls and a bottom wall;
simultaneously with imaging the cross-section of the first sample, removing a portion of each of a first plurality of samples to expose a cross-section of each of the first plurality of samples so that the cross-section of each of the first plurality of samples can be imaged, the cross-section of each of the first plurality of samples having sidewalls and a bottom wall;
after imaging the cross-section of the first sample, imaging the cross-section of at least one of the first plurality of samples; and
simultaneously with imaging the cross-section of the at least one of the first plurality of samples, preparing a cross-section of a second plurality of samples so that the cross-section of each of the second plurality of samples can be imaged, the cross-section of each of the second plurality of samples having sidewalls and a bottom wall,
wherein the first plurality of samples excludes the first sample, and the second plurality of samples excludes the first plurality of samples.

\* \* \* \* \*